(12) United States Patent
Choi et al.

(10) Patent No.: US 12,290,342 B2
(45) Date of Patent: May 6, 2025

(54) APPARATUS AND METHOD FOR ESTIMATING BIO-INFORMATION

(71) Applicant: SAMSUNG ELECTRONICS CO., LTD., Suwon-si (KR)

(72) Inventors: Chang Mok Choi, Suwon-si (KR); Tak Hyung Lee, Seoul (KR); Ho Jun Chang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 746 days.

(21) Appl. No.: 17/538,388

(22) Filed: Nov. 30, 2021

(65) Prior Publication Data

US 2023/0118582 A1  Apr. 20, 2023

(30) Foreign Application Priority Data

Oct. 7, 2021  (KR) .......................... 10-2021-0132964

(51) Int. Cl.
*A61B 5/021* (2006.01)
*A61B 5/00* (2006.01)

(52) U.S. Cl.
CPC ........ *A61B 5/02116* (2013.01); *A61B 5/7435* (2013.01); *A61B 2562/0247* (2013.01)

(58) Field of Classification Search
CPC .............. A61B 5/02116; A61B 5/7435; A61B 2562/0247
See application file for complete search history.

(56) References Cited

U.S. PATENT DOCUMENTS 11,393,257 B2   7/2022  Wang et al.
2017/0286789 A1*  10/2017  Wintergerst Lavin ......................
                                              G06V 40/1306
(Continued)

FOREIGN PATENT DOCUMENTS

KR   10-2019-0100814 A   8/2019
KR   10-2019-0107473 A   9/2019
(Continued)

OTHER PUBLICATIONS

Communication dated Mar. 31, 2023, issued by the Korean Intellectual Property Office in Korean Patent Application No. 10-2021-0132964.

(Continued)

*Primary Examiner* — Jason M Ip
(74) *Attorney, Agent, or Firm* — Sughrue Mion, PLLC

(57) ABSTRACT

An apparatus for estimating bio-information, may include: a sensor part having a photoplethysmography (PPG) sensor configured to measure a PPG signal from an object of a user, and a force sensor configured to measure a contact force between the object and the PPG sensor; an output interface, which before the PPG signal is measured, is configured to output first guide information indicating a predetermined number of times the user is required to touch the sensor part, and second guide information indicating a number of times that the sensor part has been touched since the first guide information is output; and a processor configured to estimate bio-information of the user by using the PPG signal based on the number of times that the sensor has been touched since the first guide information is output, corresponding to the predetermined number of times the user is required to touch.

13 Claims, 14 Drawing Sheets

(56) References Cited

U.S. PATENT DOCUMENTS

| | | | |
|---|---|---|---|
| 2018/0056797 A1* | 3/2018 | Cao | H01R 13/641 |
| 2018/0082102 A1* | 3/2018 | Lee | G06V 40/67 |
| 2018/0177413 A1* | 6/2018 | Kwon | A61B 5/0053 |
| 2018/0353089 A1 | 12/2018 | Choi et al. | |
| 2018/0365466 A1* | 12/2018 | Shim | G06V 40/67 |
| 2019/0274555 A1 | 9/2019 | Park et al. | |
| 2019/0313916 A1 | 10/2019 | Oh et al. | |
| 2019/0387985 A1 | 12/2019 | Kang et al. | |
| 2020/0008693 A1 | 1/2020 | Mukkamala et al. | |
| 2021/0030367 A1 | 2/2021 | Cho et al. | |

FOREIGN PATENT DOCUMENTS

| | | |
|---|---|---|
| KR | 10-2019-0120988 A | 10/2019 |
| KR | 10-2019-0143340 A | 12/2019 |
| KR | 10-2020-0025553 A | 3/2020 |
| WO | 2017/099374 A1 | 6/2017 |
| WO | 2019/159500 A1 | 8/2019 |

OTHER PUBLICATIONS

Chandrasekhar et al., "Smartphone-based blood pressure monitoring via the oscillometric finger-pressing method," Science Translational Medicine, vol. 10, eaap8674, Mar. 7, 2018, Total 12 pages.

\* cited by examiner

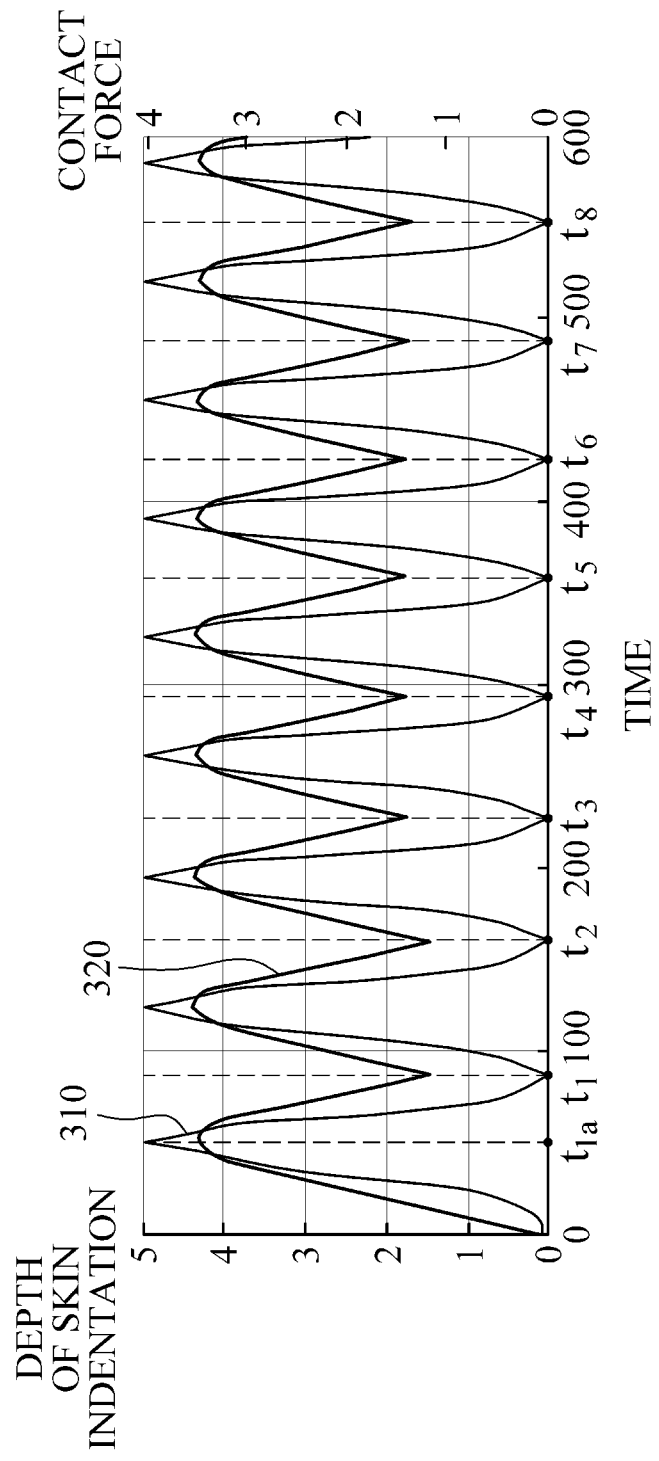

APPARATUS AND METHOD FOR ESTIMATING BIO-INFORMATION

CROSS-REFERENCE TO RELATED APPLICATION(S)

This application claims priority from Korean Patent Application No. 10-2021-0132964, filed on Oct. 7, 2021, in the Korean Intellectual Property Office, the disclosure of which is incorporated herein by reference in its entirety.

BACKGROUND

1. Field

The following description relates to an apparatus and method for non-invasively estimating bio-information.

2. Description of the Related Art

Recently, with the aging population, soaring medical costs, and a lack of medical personnel for specialized medical services, research is being actively conducted on IT-medical convergence technologies, in which IT technology and medical technology are combined. Particularly, monitoring of the health condition of the human body is not limited to medical institutions, but is expanding to mobile healthcare fields that may monitor a user's health condition anywhere and anytime in daily life at home or office. Typical examples of bio-signals, indicating the health condition of individuals, include an electrocardiography (ECG) signal, a photoplethysmogram (PPG) signal, an electromyography (EMG) signal, etc., and various bio-signal sensors have been developed to measure these signals in daily life.

SUMMARY

According to an aspect of an example embodiment, an apparatus for estimating bio-information may include: a sensor part having a photoplethysmography (PPG) sensor configured to measure a PPG signal from an object of a user, and a force sensor configured to measure a contact force between the object and the PPG sensor; an output interface, which before the PPG signal is measured, is configured to output first guide information indicating a predetermined number of times the user is required to touch the sensor part, and second guide information indicating a number of times that the sensor part has been touched since the first guide information is output; and a processor configured to estimate the bio-information of the user by using the PPG signal based on the number of times that the sensor part has been touched since the first guide information is output, corresponding to the predetermined number of times the user is required to touch.

In response to the measured contact force increasing above a first value within a first time, and then decreasing below a second value within a second time, the processor may be further configured to determine that the sensor part is touched once.

In response to the contact force not exceeding the first value within the first time, the output interface may be further configured to output third guide information indicating that the user is required to press the sensor part using a force greater than or equal to the first value.

The output interface may be further configured to display at least one of a graphic object representing the first value, a graphic object representing a measured actual contact force of the user, and a graphic object representing the third guide information.

In response to the contact force not decreasing below the second value within the second time, the output interface may be further configured to output fourth guide information for guiding the user to release the object from the sensor part.

The output interface may be further configured to display at least one of a graphic object representing an appearance of the sensor part, a graphic object representing an appearance of the object, and a graphic object representing the fourth guide information.

In response to the number of times that the sensor part has been touched since the first guide information is output, being less than the predetermined number of times, the output interface may be further configured to output fifth guide information for guiding the user to touch the sensor part again.

The output interface may be further configured to display at least one of a graphic object representing the predetermined number of times, a graphic object representing an actual number of times of contact between the object and the sensor part, a graphic object representing a required number of times of additional contact between the object and the sensor part, and a graphic object representing the fifth guide information for guiding the user to touch the sensor part again.

In response to the sensor part being touched the predetermined number of times, the output interface may be configured to output sixth guide information for guiding the user to change a pressing force while touching the sensor part with the object.

The processor may be further configured to generate an oscillometric waveform envelope based on the measured PPG signal and the contact force, and estimate the bio-information of the user based on the generated oscillometric waveform envelope.

The bio-information may be blood pressure.

According to an aspect of another example embodiment, a method of estimating bio-information may include: before measuring a PPG signal, outputting first guide information indicating a predetermined number of times a user is required to touch a sensor part with an object; determining a number of times that the sensor part has been touched since the first guide information is output; outputting second guide information indicating the determined number of times; in response to the determined number of times corresponding to the predetermined number of times, controlling a photoplethysmography (PPG) sensor to measure the PPG signal of the object; and estimating the bio-information of the user by using the measured PPG signal.

The determining the number of times that the sensor part has been touched may include: in response to a contact force between the object and the PPG sensor increasing above a first value within a first time, and then decreasing below a second value within a second time, determining that the sensor part is touched once.

The method may further include, in response to the contact force not exceeding the first value within the first time, outputting third guide information indicating that the user is required to press the sensor part using a force greater than or equal to the first value.

The outputting of the third guide information may include displaying at least one of a graphic object representing the first value, a graphic object representing a measured actual contact force of the user, and a graphic object representing the third guide information.

The method may further include, in response to the contact force not decreasing below the second value within the second time, outputting fourth guide information for guiding the user to release the object from the sensor part.

The outputting of the fourth guide information may include displaying at least one of a graphic object representing an appearance of the sensor part, a graphic object representing an appearance of the object, and a graphic object representing the fourth guide information.

The method may further include, in response to the determined number of times being less than the predetermined number of times, outputting fifth guide information for guiding the user to touch the sensor part again.

The outputting of the fifth guide information may include displaying at least one of a graphic object representing the predetermined number of times, a graphic object representing an actual number of times of contact between the object and the sensor part, a graphic object representing a required number of times of additional contact between the object and the sensor part, and a graphic object representing the fifth guide information for guiding the user to touch the sensor part again.

The method may further include, in response to the sensor part being touched the predetermined number of times, outputting sixth guide information for guiding the user to change a pressing force while touching the sensor part with the object.

BRIEF DESCRIPTION OF THE DRAWINGS

The above and/or other aspects will be more apparent by describing certain example embodiments, with reference to the accompanying drawings, in which:

FIGS. 3A to 3C are diagrams explaining a relationship between viscoelastic properties of skin tissue and a PPG signal;

DETAILED DESCRIPTION

Figure 1:
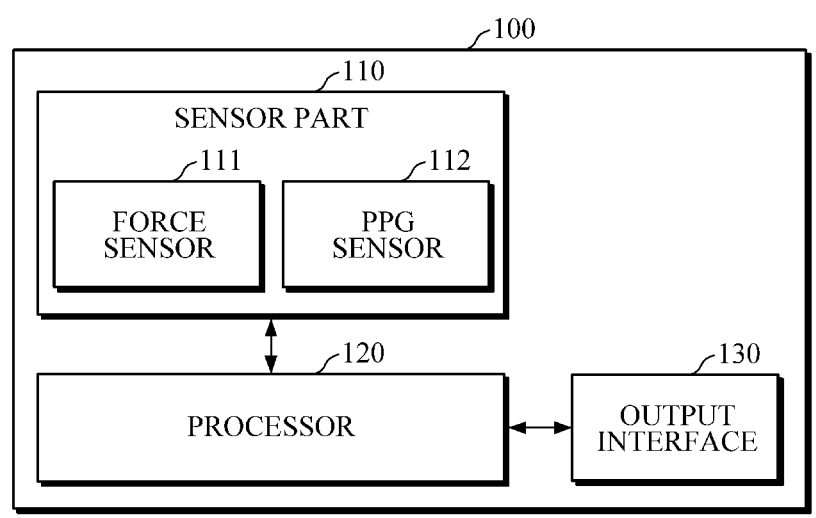
FIG. 1 is a block diagram illustrating an apparatus for estimating bio-information according to an example embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit for performing at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of an apparatus and method for estimating bio-information will be described in detail with reference to the accompanying drawings.

FIG. 1 is a block diagram illustrating an apparatus for estimating bio-information according to an example embodiment of the present disclosure. The apparatus 100 for estimating bio-information may be mounted in a wearable device worn by a user. In this case, the wearable device may be of various types, such as a wristwatch-type wearable device, a bracelet-type wearable device, a wristband-type wearable device, a ring-type wearable device, a glasses-type wearable device, a headband-type wearable device, etc., and is not particularly limited in shape or size and the like.

Referring to FIG. 1, the apparatus 100 for estimating bio-information includes a sensor part 110, a processor 120, and an output interface 130.

In this case, the bio-information may include blood pressure, blood glucose, antioxidant, lactate, alcohol, cholesterol, triglyceride, etc., but is not limited thereto. For convenience of explanation, the following description will be given using blood pressure as an example of the bio-information. The blood pressure may include mean arterial pressure (MAP), systolic blood pressure (SBP), diastolic blood pressure (DBP), and the like.

The sensor part 110 may include a force sensor 111 and a photoplethysmogram (PPG) sensor 112.

The force sensor 111 may measure a contact force between a user's object and the PPG sensor 112. The force sensor 111 may include a pressure sensor, a combination of the pressure sensor and a contact area sensor, a pressure sensor array, etc., but is not limited thereto. The force sensor 111 may be disposed on a lower end of the PPG sensor 112 in the sensor part 110, but is not limited thereto, and an arrangement position of the force sensor 111 may be changed variously.

In this case, the object may be a surface of the wrist that is adjacent to the radial artery, an upper part of the wrist where veins or capillaries are located, or peripheral parts of the body, such as fingers, toes, and the like where blood vessels are densely located. However, the object is not limited thereto.

The PPG sensor 112 may measure a photoplethysmography (PPG) signal from the object. The PPG sensor 112 may include one or more light sources for emitting light onto the object and one or more detectors for detecting light scattered or reflected from the object. The light source may include a light emitting diode (LED), a laser diode (LD), a phosphor, etc., but is not limited thereto. The detector may include a photodiode, a photo transistor, etc., but is not limited thereto, and may include a complementary metal-oxide semiconductor (CMOS) image sensor, a charge-coupled device (CCD) image sensor, and the like. The plurality of light sources may emit light of the same wavelength, or may emit light of different wavelengths. For example, the light source may emit light of a green wavelength, a blue wavelength, a red wavelength, an infrared wavelength, etc., but is not limited thereto. The plurality of detectors may be disposed at different distances from the light sources.

The output interface 130 may output the PPG signal measured by the sensor part 110, and initial guide information, additional guide information, and guide information for PPG signal measurement which are generated by the processor 120, and/or a blood pressure value estimated by the processor 120, and the like. For example, the output interface 130 may visually output data processed by the processor 130 through a display module, or may non-visually output the data by voice, vibrations, tactile sensation, and the like using a speaker module, a haptic module, or the like. In this case, a display area may be divided into two or more areas, in which the output interface 130 may output the PPG signal, a contact force, etc., in the form of various graphs in a first area, and along with the data, may output an estimated blood pressure value in a second area. In this case, if the estimated blood pressure value falls outside a normal range, the output interface 130 may output warning information in various manners, such as highlighting an abnormal value in red and the like, displaying the abnormal value along with a normal range, outputting a voice warning message, adjusting a vibration intensity, and the like.

Before the PPG signal is measured, the output interface 130 may output initial guide information indicating a predetermined number of times a user is required to touch the sensor part 110 with an object (e.g., a user's finger).

The skin tissue of the human body has viscoelastic properties, such that when the skin is pressed, it takes time for the pressed skin to return to an original state. Accordingly, a PPG signal, which is measured after touching the sensor part 110 with the object a predetermined number of times, e.g., twice or three times or less, is considerably different from a PPG signal measured after touching the sensor part 110 with the object a greater number of times. A detailed description thereof will be given with reference to FIGS. 3A to 3C.

Figure 3B:
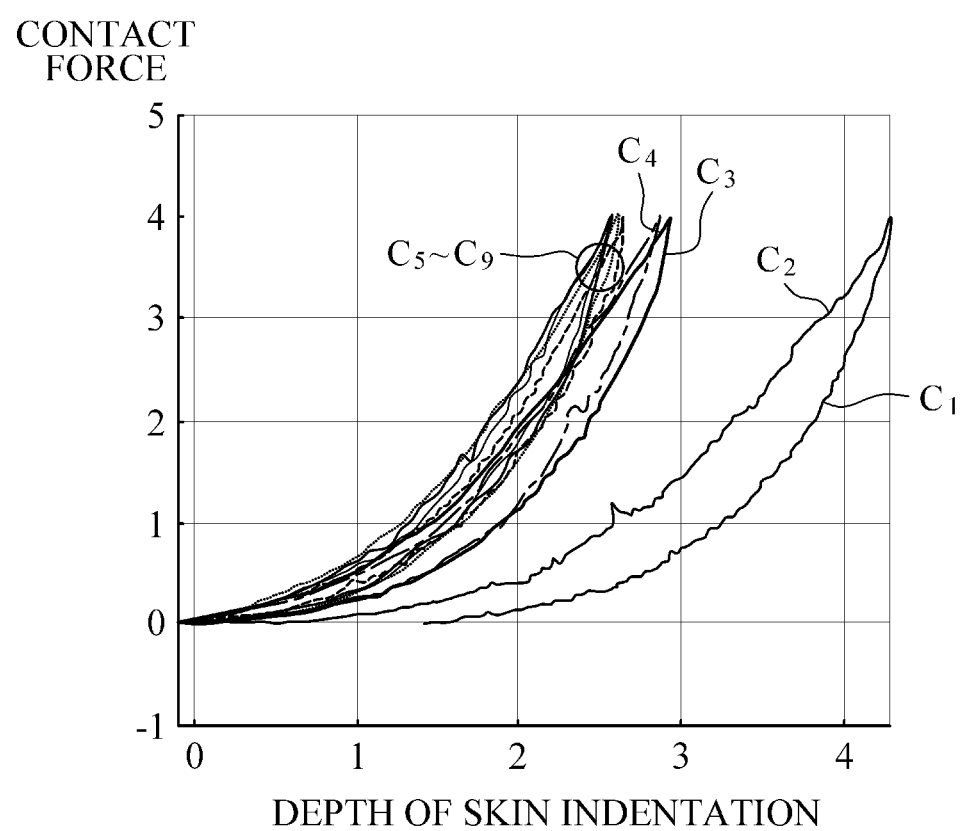
Figure 3C:
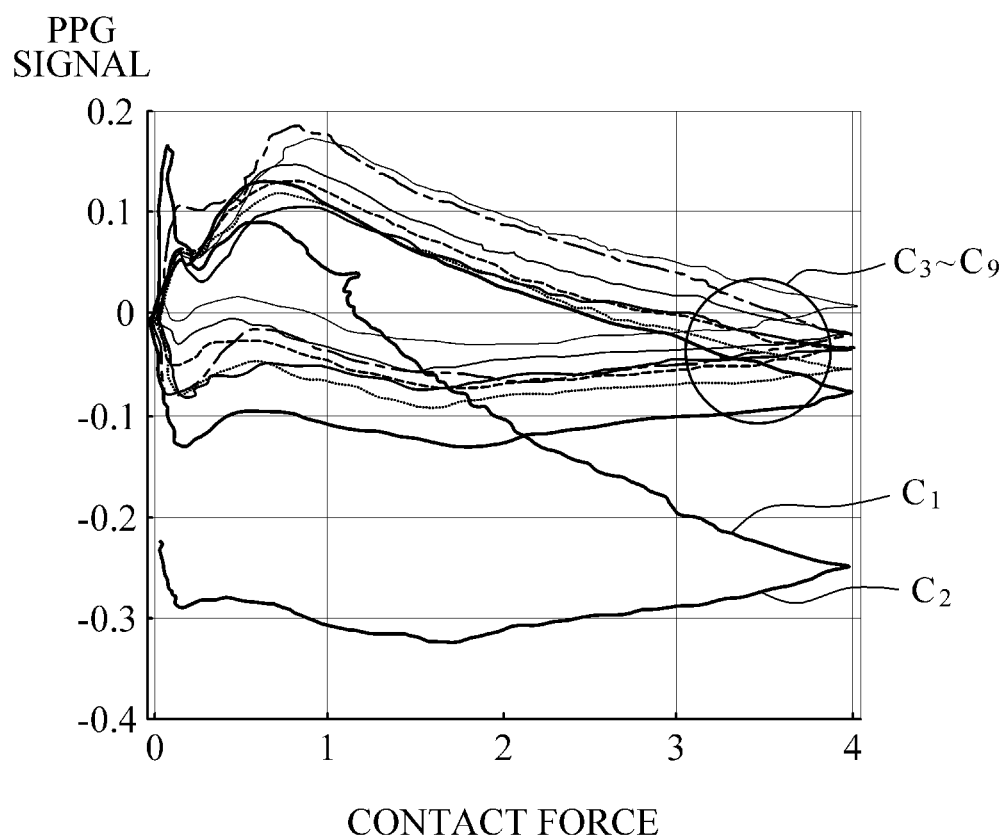

FIGS. 3A to 3C are diagrams explaining a relationship between viscoelastic properties of skin tissue and a PPG signal.

In FIG. 3A, the horizontal axis indicates time and the vertical axis indicates a contact force 310 and a depth 320 of the object pressed on the sensor part 110. The depth 30 may refer to an indentation remains after the skin of the object is pressed and released. When the contact force 310 shows a predetermined flow pattern over time, the depth 320 of the object pressed on the sensor part 110 changes over a range of from 0 to about 4 during a period of time from 0 to $t_{1a}$, e.g., when the object is pressed on the sensor part 110 for the first time, due to viscoelastic properties of the skin tissue as described above. By contrast, during a period of time from $t_{1a}$ to 600 following the time $t_{1a}$, the depth 320 of the object pressed on the sensor part 110 changes over a range of approximately from 2 to 4. That is, it can be seen that a variation in the depth 320 of the object pressed on the sensor part 110 is greater during the period of time from 0 to $t_{1a}$.

In FIG. 3B, the horizontal axis indicates a depth of the object pressed on the sensor part 110 and the vertical axis indicates a contact force, in which $C_1$ to $C_9$ respectively indicate a case where the object is pressed on the sensor part 110 for the first time to a case where the object is pressed on the sensor part 110 nine times. Referring to FIG. 3B, it can be seen that assuming that the contact force is 2, the depth of the pressed object is approximately 2 in cases $C_3$ to $C_9$, but in case $C_1$, the depth is approximately 4, and in case $C_2$, the depth is approximately 3. That is, even when the object is pressed on the sensor part 110 with the same contact force, the depth of the pressed object in the case where the contact is made for the first time or twice is greater than that in the case where the contact is made three times or more.

In FIG. 3C, the horizontal axis indicates a contact force, and the vertical axis indicates a measured PPG signal. As in the case of FIG. 3B, $C_1$ to $C_9$ respectively indicate a case where the object is pressed on the sensor part 110 for the first time to a case where the object is pressed on the sensor part 110 nine times. Referring to FIG. 3C, it can be seen that a variation in the PPG signal relative to an increase in contact force in a graph of $C_1$ greater than a variation in the PPG signal relative to an increase in contact force in graphs of $C_2$ to $C_9$.

In sum with reference to FIGS. 3A to 3C, due to viscoelastic properties of the skin tissue, there is a similarity or a predetermined pattern between PPG signals, measured after the object is pressed on the sensor part several number of times, e.g., three or more times, such that by using the PPG signals for estimating blood pressure, blood pressure may be estimated more accurately.

A detailed description of initial guide information output by the output interface 130 will be given below with reference to FIG. 4A.

Figure 4A:
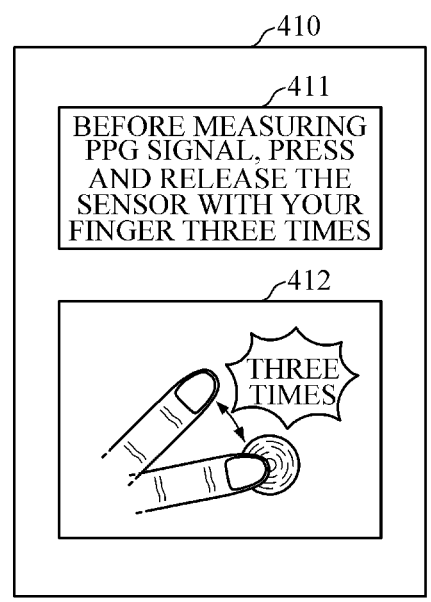
FIG. 4A is a diagram illustrating initial guide information.

FIG. 4A is a diagram illustrating initial guide information. For convenience of explanation, FIG. 4A illustrates an example in which the output interface 130 visually displays the initial guide information on a user screen 410, but the output interface 130 may also display the initial guide information in a non-visual manner by voice, vibrations, tactile sensation, and the like using a speaker module, a haptic module, or the like.

Referring to FIG. 4A, before the PPG signal is measured, the output interface 130 may display a text graphic object 411, indicating the initial guide information, and an image graphic object 412 on the user screen 410. Either the text graphic object 411, indicating the initial guide information, or the image graphic object 412 may be omitted.

Although not illustrated herein, the output interface 130 may provide additional guide information on a contact time of each contact, along with a predetermined number of times a user touches the sensor part with an object. For example, the output interface 130 may display information, such as "press and release the sensor with your finger three times for a short period of time" or "press and release the sensor with your finger three times for less than one second," and the like.

While FIG. 4A illustrates that the predetermined number of times is three times, the predetermined number of times of contact between the sensor part and the object is not limited thereto, and may be changed to various numbers. FIG. 4A illustrates that the object is a finger, but the object is not limited thereto and may be changed variously as described above.

Referring back to FIG. 1, the processor 120 may be connected electrically, mechanically, or through wired or wireless communication to the sensor part 110 and the output interface 130.

The processor 120 may determine whether the object is in contact with the sensor part 110, and/or a number of times of contact therebetween. In this case, the processor 120 may determine whether the object is in contact with the sensor part 110, and/or the number of times of contact therebetween, based on a force measurement result of the force sensor 111.

For example, if a contact force, measured by the force sensor 111, exceeds a first value within a first time and then is less than a second value within a second time, the processor 120 may determine that the object is in contact with the sensor part 110 once, but the determination is not limited thereto.

Upon determining whether the object is in contact with the sensor part 110, and/or the number of times of contact therebetween, the processor 120 may generate additional guide information if a determination result does not correspond to the initial guide information output by the output interface 130. In this case, the generated additional guide information may be output through the output interface 130. The additional guide information output by the output interface 130 will be described in detail below with reference to FIGS. 4B to 4D.

Figure 4B:
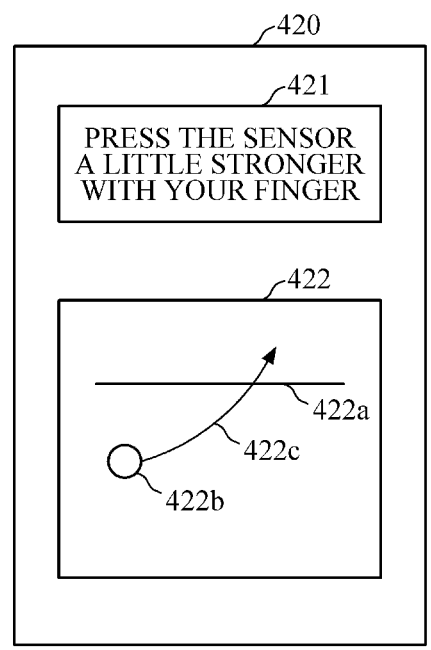
FIG. 4B is a diagram illustrating additional guide information for guiding a user to press a sensor part with an object using a force greater than or equal to a first value.

If a measured actual contact force does not exceed the first value within the first time, the output interface 130 may output additional guide information for guiding a user to press the sensor part with the object using a force greater than or equal to the first value. FIG. 4B is a diagram illustrating additional guide information for guiding a user to press the sensor part with an object using a force greater than or equal to the first value.

Referring to FIG. 4B, if an actual contact force of the object is not measured or is less than or equal to the first value, the output interface 130 may display, on the user screen 420, a text graphic object 421 for guiding the object to press the sensor part with a greater force and an image graphic object 422 for guiding the object to press the sensor part with a force greater than or equal to the first value. In this case, either the text graphic object 421 or the image graphic object 422 may be omitted.

While FIG. 4B illustrates an example in which the text graphic object 421 displays a relative force, such as "press a little stronger" and the like, but the text graphic object 421 is not limited thereto and may display, in numbers, the first value as a force to be applied by the user, the measured actual contact force of the user, and a value of force to be additionally applied by the user.

The image graphic object 422 may include a graphic object 422a representing the first value, a graphic object 422b representing the actual contact force of the user and displayed below the graphic object 422a, and a graphic object 422c for guiding the user to press the sensor part with a greater force.

The graphic object 422a representing the first value is shown in a solid line, but is not limited thereto, and may be shown in various shapes, such as a dotted line and the like. The graphic object 422c for guiding the user to press the sensor part with a greater force is shown as an arrow, but the shape is not limited thereto. In addition, the graphic object 422c for guiding the user to press the sensor part with a greater force may further include a text graphic object (not shown), such as "press the sensor part with a greater force above the reference line," along with the shape illustrated herein.

In this case, if the actual contact force of the user increases, the graphic object 422b representing the user's actual contact force may be displayed as moving in a right-upward direction, so that the user may visually recognize a change in the actual contact force.

Figure 4C:
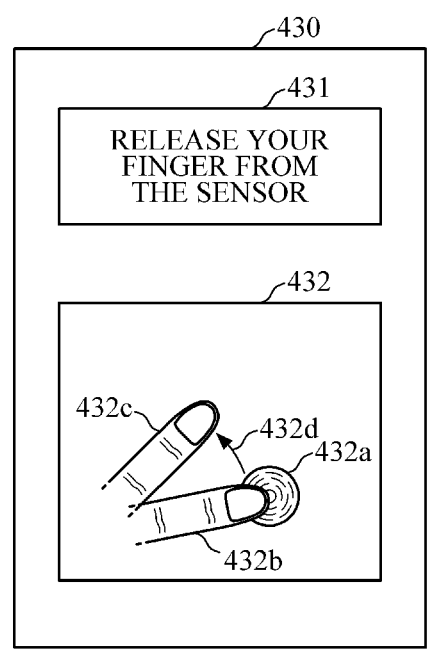
FIG. 4C is a diagram illustrating additional guide information for guiding a user to release an object from a sensor part.

If the measured actual contact force exceeds the first value within the first time and then is not less than the second value within the second time, the output interface 130 may output additional guide information for guiding the user to release the object from the sensor part. FIG. 4C is a diagram illustrating additional guide information for guiding the user to release the object from the sensor part.

Referring to FIG. 4C, the output interface 130 may display, on the user screen 430, a text graphic object 431 for guiding the user to release the object from the sensor part and an image graphic object 432. In this case, either the text graphic object 431 or the image graphic object 432 may be omitted.

The image graphic object 432 may include a graphic object 432a representing the appearance of the sensor part, graphic objects 432b and 432c representing the appearance of the object, and a graphic object 432d for guiding the user to release the object from the sensor part. In this case, reference number 432b denotes a state in which the object presses the sensor part, and reference numeral 432c denotes a state in which the user releases the object from the sensor part according to the output additional guide information. In this case, the graphic object 432d for guiding the user to release the object from the sensor part may guide the user to release the object from the sensor part by using a shape of a figure, such as an arrow, as illustrated herein. However, the graphic object 432d for guiding the user to release the object from the sensor part is not limited thereto and may further include a text graphic object as indicated by reference numeral 431.

Figure 4D:
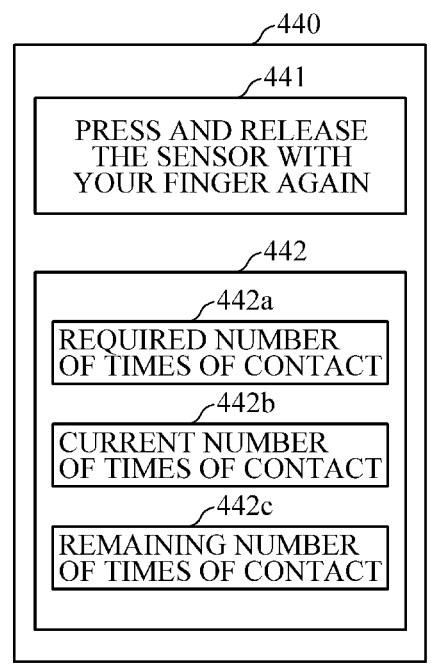
FIG. 4D is a diagram illustrating additional guide information for guiding a user to touch a sensor part again.

If a number of times of actual contact between the object and the sensor part, which is determined by the processor 120, is less than a predetermined number of times in the initial guide information, the output interface 130 may output additional guide information for guiding the user to touch the sensor part again. FIG. 4D is a diagram illustrating additional guide information for guiding the user to touch the sensor part again.

Referring to FIG. 4D, if a number of times of contact between the object and the sensor part is less than a predetermined number of times, the output interface 130 may display a text graphic object 441 for guiding the user to touch the sensor part again, and a graphic object 442 including information on the number of times of contact. In this case, either the text graphic object 441 for guiding the user to touch the sensor part again and the graphic object 442 including information on the number of times of contact may be omitted.

Referring to FIG. 4D, the text graphic object 441 for guiding the user to touch the sensor part again does not display a required number of times of additional contact, but the text graphic object 441 is not limited thereto, and may include information on the additional contact, such as "please touch the sensor part two more times."

The graphic object 442 including information on the number of times of contact may include a graphic object 442a representing a required predetermined number of times of contact, a graphic object 442b representing a current number of times of contact which is actually measured, and a graphic object 442c representing a remaining number of times of contact. While FIG. 4D illustrates an example in which the graphic object 442 representing information on the number of times of contact is a text graphic object, but the graphic object 442 is not limited thereto and may be a graphic object such as a figure, an image, and the like.

Referring back to FIG. 1, the processor 120 may control the sensor part 110 in response to a user's request, and/or based on determination thereof.

For example, if the determined number of times of contact satisfies a predetermined number of times, the processor 120 may control the PPG sensor 112 to acquire a PPG signal. In this case, the output interface 130 may output guide information on measurement of the PPG signal. The guide information on measurement of the PPG signal, which is output by the output interface 130, will be described below with reference to FIG. 4E.

Figure 4E:
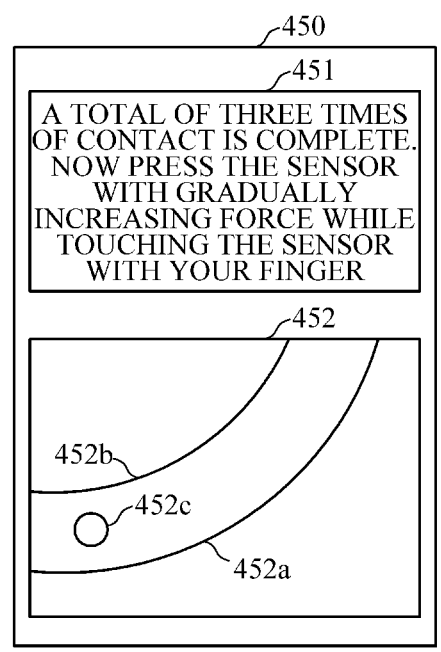
FIG. 4E is a diagram illustrating guide information on measurement of a PPG signal.

FIG. 4E is a diagram illustrating guide information on measurement of a PPG signal.

Referring to FIG. 4E, once a predetermined number of times of contact is complete, the output interface 130 may display, on a user screen 450, a graphic object 451 representing guide information on measurement of the PPG signal, and an image graphic object 452.

Although not illustrated in FIG. 4E, the text graphic object 451 may further include a time during which the user is required to press the sensor part with a gradually increasing force while touching the sensor part with a finger.

The image graphic object 452 may include a graphic object 452a representing a lower limit of a pre-defined reference contact force, a graphic object 452b representing an upper limit thereof, and a graphic object 452c representing a measured actual contact force. In this case, as illustrated herein, the graphic objects 452a and 452b representing the lower and upper limits of the pre-defined reference contact force may include lines or continuous points, a circular shape, an elliptical shape, a polygonal shape, etc., and the graphic object 452c representing the measured actual contact force may include a circular shape, an elliptical shape, a polygonal shape, a cross, an arrow, and the like.

As illustrated in FIG. 4E, the output interface 130 may change the graphic objects 452a and 452b, representing the lower and upper limits of the pre-defined reference contact force, to a shape that is gradually curved in a right-upward direction so that the user may gradually increase a pressing force of the finger over time.

While FIG. 4E illustrates an example in which the text graphic object 451, representing the guide information on measurement of the PPG signal, and the image graphic object 452 provide information for guiding the object to press the sensor part with a gradually increasing force over time, but the guide information is not limited thereto, and may be guide information for guiding the user to gradually decrease the pressing force after pressing the sensor part with a force greater than or equal to a predetermined threshold value.

Referring back to FIG. 1, the processor 120 may estimate a user's blood pressure based on the acquired PPG signal.

In this case, upon receiving the PPG signal from the sensor part 110, the processor 120 may perform preprocessing, such as filtering for removing noise from the PPG signal, amplifying the PPG signal, converting the PPG signal into a digital signal, and the like. For example, the processor 120 may perform band-pass filtering between 0.4 Hz and 10 Hz by using a band-pass filter, to remove noise from the PPG signal received from the sensor part 110. Further, the processor 120 may correct the PPG signal by reconstructing the PPG signal based on Fast Fourier Transform. However, the preprocessing is not limited thereto, and the processor 120 may perform various other preprocessing operations according to various measurement environments, such as computing performance or measurement accuracy of a device, purpose of bio-information estimation, a measured portion of a user, temperature and humidity of an object, temperature of the sensor part, and the like.

The processor 120 may generate an oscillometric waveform envelope based on the measured PPG signal and the contact force, and may estimate blood pressure based on the generated oscillometric waveform envelope.

For example, the processor 120 may detect a pulse peak and a pulse onset at each time point of the PPG signal, and may extract a peak-to-peak point of the PPG signal by subtracting an amplitude value at the pulse onset from an amplitude value at the detected pulse peak. In this case, the processor 120 may generate the oscillometric waveform envelope, which represents contact force versus PPG signal, by plotting the peak-to-peak amplitude at each measurement time point against a contact force value at a corresponding time point.

The processor 120 may preprocess the generated oscillometric waveform envelope. For example, the processor 120 may smooth the generated oscillometric waveform envelope. In this case, the processor 120 may smooth the generated oscillometric waveform envelope by using a moving sum, a moving average, polynomial fitting, Gaussian fitting, and the like. In another example, the processor 120 may obtain a derivative signal by taking a derivative of the obtained oscillometric waveform envelope or the smoothed oscillometric waveform envelope. In yet another example, the processor 120 may normalize the generated oscillometric waveform envelope. However, the processor 120 is not limited thereto.

The processor 120 may extract one or more features from the generated oscillometric waveform envelope and/or the preprocessed oscillometric waveform envelope and may estimate a user's blood pressure based on the extracted features.

For example, the processor 120 may extract, as features, an amplitude value or a contact force value at a maximum peak point of the generated oscillometric waveform envelope, or contact force values located before and after the maximum peak point and having a preset ratio (e.g., 0.5 to 0.7) to the contact force value at the maximum peak point.

Upon extracting one or more features from the oscillometric waveform envelope, the processor 120 may estimate a user's blood pressure by using a pre-defined bio-information estimation model as represented by the following Equation 1.

$$y = ax + b \qquad \text{[Equation 1]}$$

Herein, y denotes bio-information to be obtained, e.g., diastolic blood pressure (DBP), systolic blood pressure (SBP), mean arterial blood pressure (MAP), and the like; x denotes the extracted feature value; and a and b denote values pre-calculated by preprocessing, and may be defined differently depending on the type of bio-information, e.g., DBP, SBP, MAP, and the like, but are not limited thereto and may be pre-generated in the form of a table in which blood pressure values are mapped to feature values.

Figure 2:
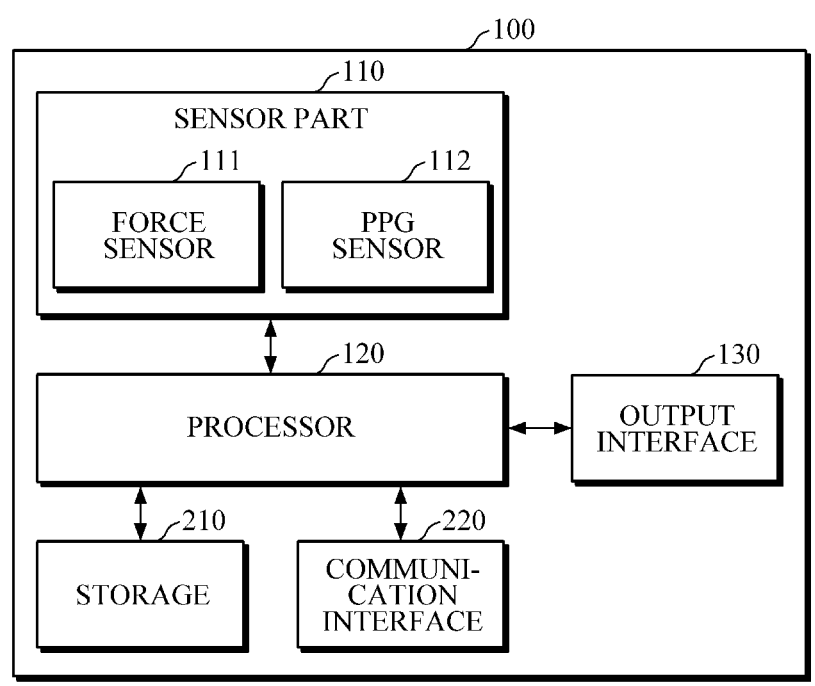
FIG. 2 is a block diagram illustrating an apparatus for estimating bio-information according to another example embodiment of the present disclosure.

FIG. 2 is a block diagram illustrating an apparatus 200 for estimating bio-information according to another example embodiment of the present disclosure. Referring to FIG. 2, the apparatus 200 for estimating bio-information may further include a storage 210 and a communication interface 220 in addition to the sensor part 110, the processor 120, and the output interface 130 described above. The sensor part 110, the processor 120, and the output interface 130 are described above with reference to FIG. 1, such that the storage 210 and the communication interface 220 will be described in detail below.

The storage 210 may store processing results of the sensor part 110 and/or the processor 120. For example, the storage 210 may store the measured PPG signal, the generated oscillometric waveform envelope, the estimated blood pressure value, and the like. In addition to the data, the storage 210 may store a variety of reference information required for estimating blood pressure. For example, the reference information may include user characteristic information, such as a user's age, gender, health condition, and the like. Further, the reference information may include a blood pressure estimation model, criteria for estimating blood pressure, a calibration cycle, a reference force set for each user, and/or reference distribution of force, and the like, but is not limited thereto.

In this case, the storage 210 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 220 may communicate with an external device by using wired or wireless communication techniques under the control of the processor 120, and may transmit and receive various data to and from the external device. For example, the communication interface 220 may transmit a blood pressure estimation result to the external device, and may receive a variety of reference information required for estimating blood pressure, e.g., user characteristic information, such as a user's age, gender, health condition, and the like, from the external device. In this case, the external device may include an information processing device, such as a cuff-type blood pressure measuring device, a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 5:
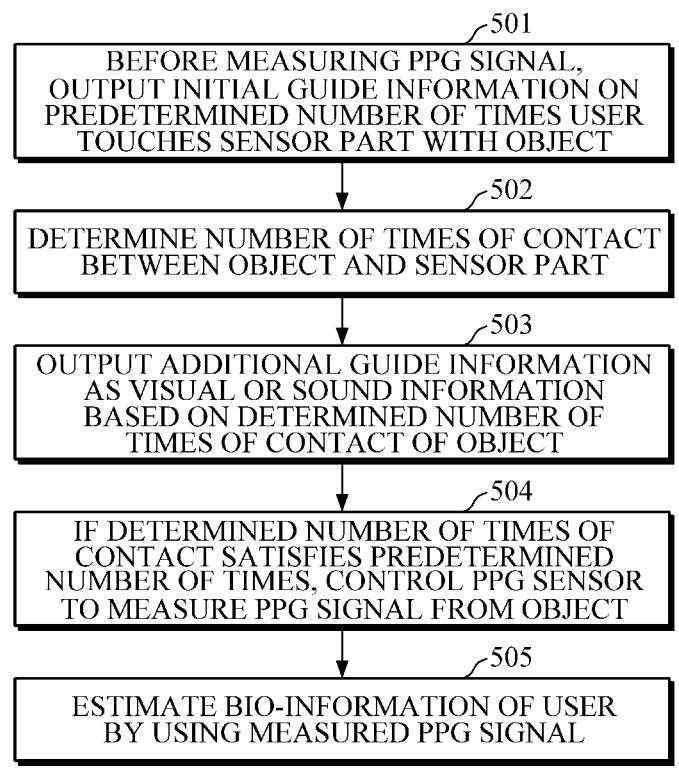
FIG. 5 is a flowchart illustrating a method of estimating bio-information according to an example embodiment of the present disclosure.

FIG. 5 is a flowchart illustrating a method of estimating bio-information according to an example embodiment of the present disclosure. The method of FIG. 5 is an example of a method of estimating bio-information performed by the apparatuses 100 and 200 for estimating bio-information of FIGS. 1 and 2, which is described in detail above, and thus will be briefly described below in order to avoid redundancy.

First, before measuring a PPG signal, the apparatus for estimating bio-information may output initial guide information on a predetermined number of times a user touches the sensor part with an object in operation 501. In this case, the initial guide information may include at least one of a text graphic object for guiding a predetermined number of times of contact between the object and the sensor part, and an image graphic object.

Then, the apparatus for estimating bio-information may determine a number of times of contact between the object and the sensor part in operation 502. In this case, the apparatus for estimating bio-information may determine a number of times of contact between the object and the sensor part based on a force measurement result of the force sensor. For example, if the measured contact force exceeds the first value within the first time and then is less than the second value within the second time, the apparatus for estimating bio-information may determine that the object is in contact with the sensor part once.

Subsequently, the apparatus for estimating bio-information may output additional guide information as visual or sound information based on the determined number of times of contact of the object in operation 503. For example, upon determining whether the object is in contact with the sensor part, and/or the number of times of contact, if a determination result does not correspond to the initial guide information, the apparatus for estimating bio-information may generate additional guide information. In this case, the additional guide information may include at least one of a text graphic object, representing whether the object is in contact with the sensor part and/or the number of times of contact, and an image graphic object.

Next, if the determined number of times of contact satisfies the predetermined number of times, the apparatus for estimating bio-information may control the PPG sensor to measure a PPG signal from the object in operation 504. In this case, the apparatus for estimating bio-information may output guide information on measurement of the PPG signal.

Then, the apparatus for estimating bio-information may estimate bio-information of a user by using the measured PPG signal in operation 505. In this case, the apparatus for estimating bio-information may generate an oscillometric waveform envelope based on the measured PPG signal and the contact force, and may estimate blood pressure of the user based on the generated oscillometric waveform envelope. A detailed description thereof will be omitted.

Figure 6:
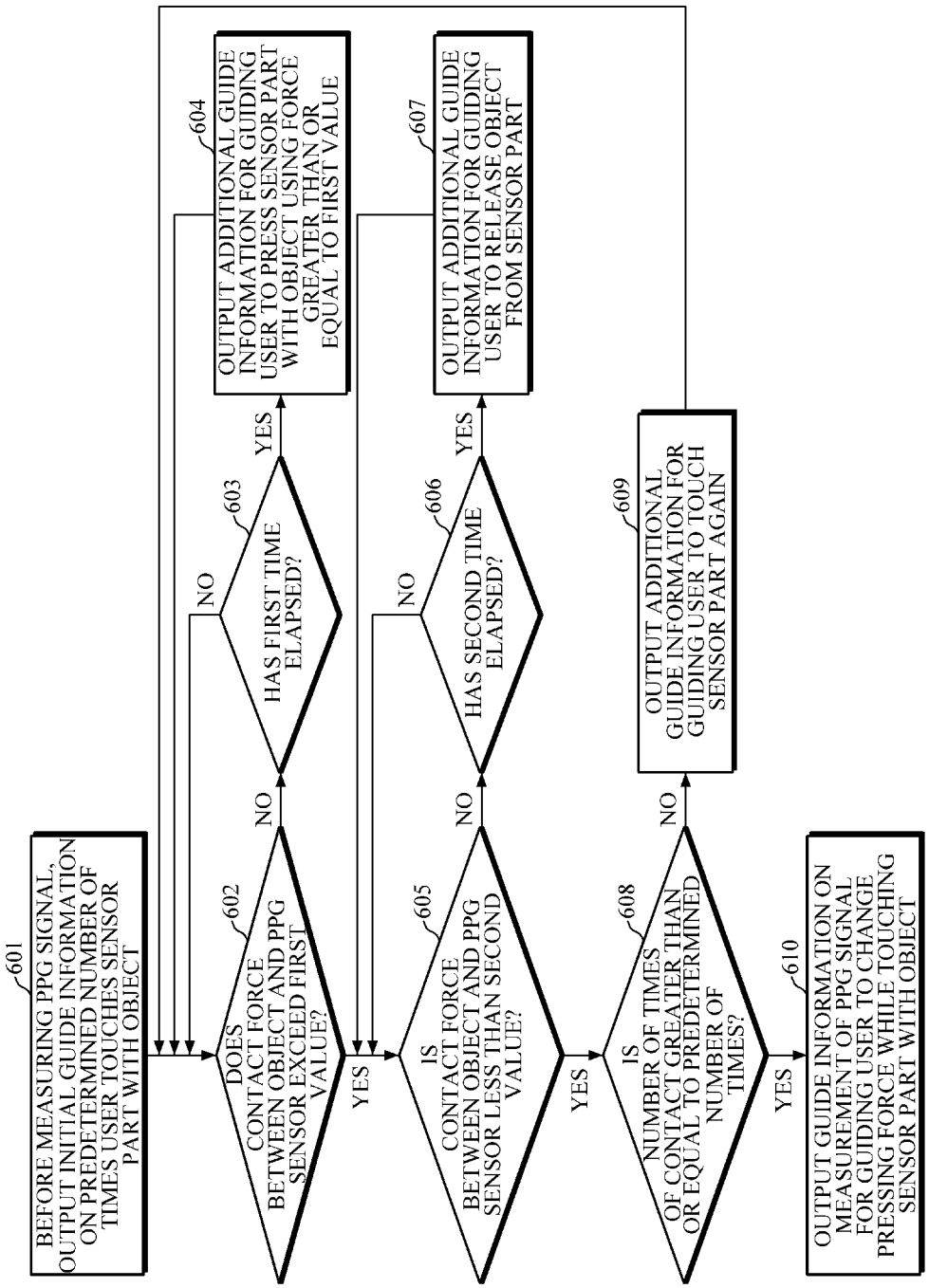
FIG. 6 is a flowchart illustrating a method of estimating bio-information according to another example embodiment of the present disclosure.

FIG. 6 is a flowchart illustrating a method of estimating bio-information according to another example embodiment of the present disclosure. The method of FIG. 6 is an example of a method of estimating bio-information performed by the apparatuses 100 and 200 for estimating bio-information of FIGS. 1 and 2, which is described above in detail, and thus will be briefly described below in order to avoid redundancy.

First, before measuring the PPG signal, the apparatus for estimating bio-information may output initial information on a predetermined number of times a user touches the sensor part with an object in operation 601.

Then, the apparatus for estimating bio-information may determine whether a contact force between the object and the PPG sensor exceeds a first value in operation 602.

Upon determination, if the contact force does not exceed the first value, the apparatus for estimating bio-information may determine whether the first time has elapsed in operation 603.

Upon determination, if the first time has elapsed, the apparatus for estimating bio-information may output additional guide information for guiding the user to press the sensor part with the object using a force greater than or equal to the first value in operation 604. In this case, the additional guide information for guiding the object to press the sensor part with the force greater than or equal to the first value may include at least one of a graphic object representing the first value, a graphic object representing the measured actual contact force of the user, and a graphic object representing the additional guide information for guiding the user to press the sensor part a force greater than or equal to the first value.

Subsequently, if the contact force exceeds the first value within the first time, the apparatus for estimating bio-information may determine whether the contact force between the object and the PPG sensor is less than a second value in operation 605.

Upon determination, if the contact force is not less than the second value, the apparatus for estimating bio-information may determine whether a second time has elapsed in operation 606.

Upon determination, if the second time has elapsed, the apparatus for estimating bio-information may output additional guide information for guiding the user to release the object from the sensor part in operation 607. In this case, the additional guide information for guiding the user to release the object from the sensor part may include a graphic object representing the appearance of the sensor part, a graphic object representing the appearance of the object, and a graphic object representing additional guide information for guiding the user to release the object from the sensor part.

If the measured contact force exceeds the first value within the first time, and then is less than the second value within the second time, the apparatus for estimating bio-information may determine that the object is in contact with the sensor part once.

Then, the apparatus for estimating bio-information may determine whether the determined number of times of contact is greater than or equal to a predetermined number of times in the initial guide information in operation 608.

Upon determination, if the determined number of times of contact is less than the predetermined number of times, the apparatus for estimating bio-information may output additional guide information for guiding the user to touch the sensor part again in operation 609. In this case, the additional guide information for guiding the user to touch the sensor part again may include at least one of a graphic object representing the predetermined number of times, a graphic object representing an actual number of times of contact between the object and the sensor part, a graphic object representing a required number of times of additional contact, and a graphic object representing additional guide information for guiding the user to touch the sensor part again.

Upon determination, if the number of times of contact is greater than or equal to the predetermined number of times, the apparatus for estimating bio-information may output guide information on measurement of the PPG signal for guiding the user to change a pressing force while touching the sensor part with the object in operation 610. In this case, the guide information on measurement of the PPG signal may include a text graphic object and/or an image graphic object for guiding the object to press the sensor part with a gradually increasing force over time, or for guiding the object to gradually decrease a pressing force after pressing the sensor part with a force greater than or equal to a predetermined threshold value.

Figure 7:
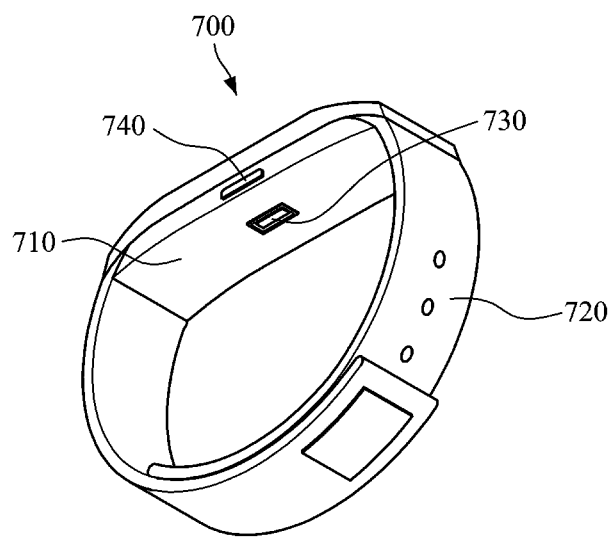
FIG. 7 is a diagram illustrating a wearable device according to an example embodiment of the present disclosure.

FIG. 7 is a diagram illustrating a wearable device according to an example embodiment of the present disclosure. The wearable device 700 may include various embodiments of the aforementioned apparatuses 100 and 200 for estimating bio-information.

Referring to FIG. 7, the wearable device 700 includes a main body 710 and a strap 720.

The strap 720 may be connected to both ends of the main body 710, and may be flexible so as to be wrapped around a user's wrist. The strap 720 may be composed of a first strap and a second strap which are separated from each other. One ends of the first strap and the second strap are connected to the main body 710, and the other ends thereof may be connected to each other via a fastening means. In this case, the fastening means may be formed as magnetic fastening, Velcro fastening, pin fastening, and the like, but is not limited thereto. Further, the strap 720 is not limited thereto, and may be integrally formed as a non-detachable band.

In this case, air may be injected into the strap 720 or the strap 720 may be provided with an air bladder, so as to have elasticity according to a change in pressure applied to the wrist, and the change in pressure of the wrist may be transmitted to the main body 710.

A battery may be embedded in the main body 710 or the strap 720 to supply power to the wearable device 700.

In addition, the sensor part 730 may be mounted on one side of the main body 710. The sensor part 730 may include a force sensor, a PPG sensor, an impedance sensor, a motion sensor, a gyro sensor, and the like. In this case, the PPG sensor may include a light source and a CIS image sensor.

The processor may be mounted in the main body 710. The processor may determine whether the object is in contact with the sensor part 730 and/or a number of times of contact therebetween based on a force measurement result of the force sensor included in the sensor part 730. For example, if the contact force measured by the force sensor exceeds the first value within the first time and then is less than the second value within the second time, the processor may determine that the object is in contact with the sensor part once, but is not limited thereto. A detailed description thereof will be omitted.

If the determined number of times of contact satisfies a predetermined number of times, the processor may control the PPG sensor, included in the sensor part 730, to acquire the PPG signal. The processor may generate an oscillometric waveform envelope based on the measured PPG signal and the contact force, and may estimate a user's blood pressure based on the generated oscillometric waveform envelope. A detailed description thereof will be omitted.

An output interface may be mounted on a front surface of the main body 710. The output interface may output initial guide information on the number of times the user touches the sensor part 730 with the object before the PPG signal is measured, and additional guide information based on the number of times of contact of the object, which is determined by the processor, and once the predetermined number of times of contact is complete, the output interface may output guide information on measurement of the PPG signal for guiding the user to change a pressing force while touching the sensor part 730 with the object, and/or a blood pressure estimation result. A detailed description thereof will be omitted.

A storage may be included in the main body 710, and may store information processed by the processor and reference information for estimating blood pressure.

In addition, the wearable device 700 may include a manipulator 740 for receiving a user's control command and transmitting the received control command to the processor. The manipulator 740 may be provided on a side surface of the main body 710, and may have a function of turning on/off the wearable device 700.

Moreover, the main body 710 may include a communication interface for transmitting and receiving data with an external device, and various other modules for performing additional functions provided by the wearable device 700.

Figure 8:
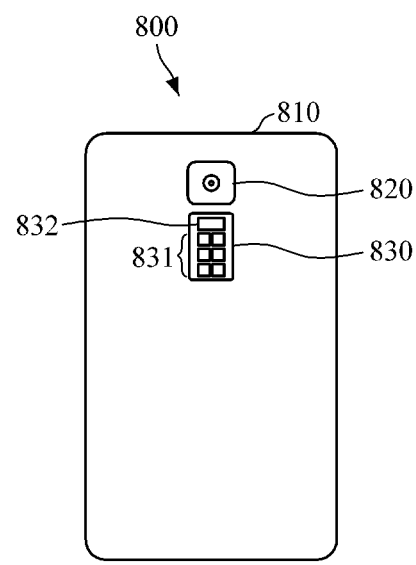
FIG. 8 is a diagram illustrating a smart device according to an example embodiment of the present disclosure.

FIG. 8 is a diagram illustrating a smart device according to an example embodiment of the present disclosure. In this case, the smart device 800 may include various embodiments of the aforementioned apparatuses 100 and 200 for estimating bio-information. In this case, the smart device may include a smartphone, a tablet PC, and the like.

Referring to FIG. 8, the smart device 800 includes a main body 810 and a sensor part 830 mounted on one surface of the main body 810. The sensor part 830 may include a force sensor and a PPG sensor, in which the PPG sensor may include one or more light sources 831 and a detector 832. In this case, the detector 832 may include a CIS image sensor. As illustrated in FIG. 8, the sensor part 830 may be mounted on a rear surface of the main body 810, but is not limited thereto. Further, the sensor part 830 may include an auxiliary sensor, such as an impedance sensor, a motion sensor, a gyro sensor, and the like.

The processor may be mounted in the main body 810. The processor may determine whether the object is in contact with the sensor part 830 and/or a number of times of contact therebetween based on a force measurement result of the force sensor included in the sensor part 730. If the determined number of times of contact satisfies a predetermined number of times, the processor may control the PPG sensor to acquire the PPG signal. The processor may generate an oscillometric waveform envelope based on the measured PPG signal and the contact force, and may estimate a user's blood pressure based on the generated oscillometric waveform envelope. A detailed description thereof will be omitted.

The main body 810 may include an image sensor 820 as illustrated in FIG. 8. When a user's object, e.g., a finger, approaches the sensor 830 to measure a PPG signal, the image sensor 820 may capture an image of the finger and may transmit the captured image to the processor. In this case, based on the image of the finger, the processor may identify a relative position of the finger with respect to an actual position of the sensor 830, and may provide a graphic object including guide information on the relative position of the finger to the user through the output interface.

In addition, a storage, a communication interface, and the like may be included in the main body 810, which may store blood pressure values estimated by the processor 810 or may transmit the values to other external devices. Various other modules for performing various functions may be mounted in the main body 810.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating blood pressure, the apparatus comprising:
   a sensor part having a photoplethysmography (PPG) sensor configured to measure a PPG signal from an object of a user, and a force sensor configured to measure a contact force between the object and the PPG sensor;
   a display, which before the PPG signal is measured, is configured to output first guide information indicating a predetermined number of times the user is required to touch the sensor part and indicating a contact time of each contact, wherein the predetermined number of times is one of three to nine times; and
   a processor configured to estimate the blood pressure of the user by using the PPG signal based on the number of times that the sensor part has been touched since the first guide information is output, corresponding to the predetermined number of times the user is required to touch,
   wherein in response to the measured contact force increasing above a first value within a first time, and then decreasing below a second value within a second time, the processor is further configured to determine that the sensor part is touched once,
   wherein in response to the contact force not exceeding the first value within the first time, the display is further configured to output second guide information indicating that the user is required to press the sensor part using a force greater than or equal to the first value,
   wherein the second guide information comprises a text graphic object and an image graphic object for guiding the object to press the sensor part, and
   wherein the image graphic object comprises a first graphic object representing the first value, a second graphic object representing an actual contact force of the user, and a third graphic object for guiding the user to press the sensor part with a greater force.

2. The apparatus of claim 1, wherein in response to the contact force not decreasing below the second value within the second time, the display is further configured to output third guide information for guiding the user to release the object from the sensor part.

3. The apparatus of claim 2, wherein the display is further configured to display at least one of a graphic object representing an appearance of the sensor part, a graphic object representing an appearance of the object, and a graphic object representing the third guide information.

4. The apparatus of claim 1, wherein in response to the number of times that the sensor part has been touched since the first guide information is output, being less than the predetermined number of times, the display is further configured to output fourth guide information for guiding the user to touch the sensor part again.

5. The apparatus of claim 4, wherein the display is further configured to display at least one of a graphic object representing the predetermined number of times, a graphic object representing an actual number of times of contact between the object and the sensor part, a graphic object representing a required number of times of additional contact between the object and the sensor part, and a graphic object representing the fourth guide information for guiding the user to touch the sensor part again.

6. The apparatus of claim 1, wherein in response to the sensor part being touched the predetermined number of times, the display is configured to output fifth guide information for guiding the user to change a pressing force while touching the sensor part with the object.

7. The apparatus of claim 6, wherein the processor is further configured to generate an oscillometric waveform envelope based on the measured PPG signal and the contact force, and estimate the blood pressure of the user based on the generated oscillometric waveform envelope.

8. A method of estimating blood pressure, the method comprising:
   before measuring a PPG signal, outputting first guide information indicating a predetermined number of times a user is required to touch a sensor part with an object and indicating a contact time of each contact, wherein the predetermined number of times is one of three to nine times;
   determining a number of times that the sensor part has been touched since the first guide information is output;
   in response to the determined number of times corresponding to the predetermined number of times, controlling a photoplethysmography (PPG) sensor to measure the PPG signal of the object; and
   estimating the blood pressure of the user by using the measured PPG signal,
   wherein the determining the number of times that the sensor part has been touched comprises:
   in response to a contact force between the object and the PPG sensor increasing above a first value within a first time, and then decreasing below a second value within a second time, determining that the sensor part is touched once,
   in response to the contact force not exceeding the first value within the first time, outputting second guide information indicating that the user is required to press the sensor part using a force greater than or equal to the first value,
   wherein the second guide information comprises a text graphic object and an image graphic object for guiding the object to press the sensor part, and
   wherein the image graphic object comprises a first graphic object representing the first value, a second graphic object representing an actual contact force of the user, and a third graphic object for guiding the user to press the sensor part with a greater force.

9. The method of claim 8, further comprising, in response to the contact force not decreasing below the second value within the second time, outputting third guide information for guiding the user to release the object from the sensor part.

10. The method of claim 9, wherein the outputting of the third guide information comprises displaying at least one of a graphic object representing an appearance of the sensor part, a graphic object representing an appearance of the object, and a graphic object representing the third guide information.

11. The method of claim 8, further comprising, in response to the determined number of times being less than the predetermined number of times, outputting fourth guide information for guiding the user to touch the sensor part again.

12. The method of claim 11, wherein the outputting of the fourth guide information comprises displaying at least one of a graphic object representing the predetermined number of times, a graphic object representing an actual number of times of contact between the object and the sensor part, a graphic object representing a required number of times of additional contact between the object and the sensor part, and a graphic object representing the fourth guide information for guiding the user to touch the sensor part again.

13. The method of claim 8, further comprising, in response to the sensor part being touched the predetermined number of times, outputting fifth guide information for guiding the user to change a pressing force while touching the sensor part with the object.

\* \* \* \* \*